United States Patent [19]

Poetsch et al.

[11] Patent Number: 5,308,542
[45] Date of Patent: May 3, 1994

[54] 4,4'-DISUBSTITUTED 2',3-DIFLUOROBISPHENYLS AND A LIQUID-CRYSTALLINE MEDIUM

[75] Inventors: Eike Poetsch, Mühltal; Volker Reiffenrath, Rossdorf; Reinhard Hittich, Modautal, all of Fed. Rep. of Germany; Bernhard Rieger, Wacore-Tamagawagakuen, Japan

[73] Assignee: Merck Patent Gesellschaft mit beschrankter Haftung, Darmstadt, Fed. Rep. of Germany

[21] Appl. No.: 688,490

[22] PCT Filed: Mar. 5, 1991

[86] PCT No.: PCT/EP91/00411
§ 371 Date: May 20, 1991
§ 102(e) Date: May 20, 1991

[87] PCT Pub. No.: WO91/13850
PCT Pub. Date: Sep. 19, 1991

[30] Foreign Application Priority Data

Mar. 13, 1990 [DE] Fed. Rep. of Germany ....... 4007863
Oct. 26, 1990 [DE] Fed. Rep. of Germany ....... 4034124

[51] Int. Cl.$^5$ ............ C09K 19/30; C09K 19/12; C07C 25/13; G02F 1/13
[52] U.S. Cl. ............ 252/299.63; 252/299.66; 570/127; 359/103
[58] Field of Search ........ 252/299.01, 299.63, 252/299.66; 359/103; 570/127

[56] References Cited

U.S. PATENT DOCUMENTS

| | | | |
|---|---|---|---|
| 4,393,231 | 7/1983 | Misaki et al. | 252/299.5 |
| 4,405,488 | 9/1983 | Sugimori et al. | 252/299.63 |
| 4,512,636 | 4/1985 | Andrews et al. | 252/299.61 |
| 4,630,897 | 12/1986 | Andrews et al. | 252/299.61 |
| 4,797,228 | 1/1989 | Goto et al. | 252/299.63 |
| 4,871,470 | 10/1989 | Wachtler et al. | 252/299.63 |
| 5,032,313 | 7/1991 | Goto et al. | 252/299.63 |
| 5,122,295 | 6/1992 | Weber et al. | 252/299.01 |
| 5,174,920 | 12/1992 | Iijima | 252/299.01 |

FOREIGN PATENT DOCUMENTS

| | | |
|---|---|---|
| 0193191 | 9/1986 | |
| 0256636 | 2/1988 | European Pat. Off. |
| 0387032 | 9/1990 | European Pat. Off. |
| 55-157523 | 12/1980 | Japan |
| 58-18326 | 2/1983 | Japan |
| 88/08441 | 2/1983 | PCT Int'l Appl. |
| 2162515 | 2/1986 | United Kingdom |

*Primary Examiner*—Shean C. Wu
*Attorney, Agent, or Firm*—Millen, White, Zelano, & Branigan

[57] ABSTRACT

The invention relates to 4,4'-disubstituted 2',3-difluorobiphenyls of the formula I

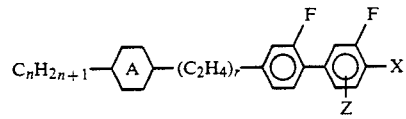

in which n is 1 to 7, A is trans-1,4-cyclohexylene or 1,4-phenylene, r is 0 or 1, X is F, Cl, —CF$_3$, —CHF$_2$, —OCF$_3$ or —OCHF$_2$ and Z is H or F.

10 Claims, No Drawings

4,4'-DISUBSTITUTED 2',3-DIFLUOROBISPHENYLS AND A LIQUID-CRYSTALLINE MEDIUM

SUMMARY OF THE INVENTION

The invention relates to novel 4,4'-disubstituted 2',3-difluorobiphenyls of the formula I

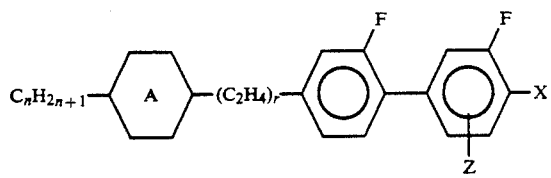

in which n is 1 to 7, A is trans1,4-cyclohexylene (Cy) or 1,4-phenylene (Ph), r is 0 or 1, Z is F, Cl, —CF₃, —CHF₂, —OCF₃ or —OCHF₂ and Z is H or F.

DE-A 30 42 391 and EP-A 0 256 636 give general formulae which cover some of the compounds according to the invention. However, neither specific derivatives of 2',3-difluorobiphenyl nor the advantageous actions thereof as components of liquid-crystalline media are described therein.

Like similar compounds, for example known from DE-A 30 42 391, the compounds of the formula I can be used as components of liquid-crystalline media, in particular for displays based on the principle of the twisted cell.

The substances employed hitherto for this purpose all have certain disadvantages, for example excessively high melting points, excessively low clearing points, inadequate stability to the action of heat, light or electrical fields, inadequate electrical resistance, or excessive dependence of the threshold voltage on temperature.

In particular in displays of the supertwist type (STN) having twist angles of significantly greater than 220°, or in displays having an active matrix, the materials employed hitherto have disadvantages.

The invention had the object of finding novel liquid-crystalline compounds which are suitable as components of liquid-crystalline media, in particular for nematic media having positive dielectric anisotropy, and which do not have the disadvantages of the known compounds, or only do so to a lesser extent. This object has been achieved by the provision of the novel compounds of the formula I.

It has been found that the compounds of the formula I are eminently suitable as components of liquidcrystalline media. In particular, they can be used to obtain liquid-crystalline media having broad nematic ranges, high clearing point and high dielectric anisotropy, excellent nematogeneity down to low temperatures, excellent chemical stability, pronounced ε⊥ at positive dielectric anisotropy, low temperature dependence of the threshold voltage and/or low optical anisotropy. In addition, the novel compounds have good solubility for other components of media of this type and high positive dielectric anisotropy at the same time as favorable viscosity.

The compounds of the formula I make it possible to produce both STN displays having a vary steep electrooptical characteristic line and displays having an active matrix with excellent long-term stability.

In the pure state, the compounds of the formula I are color less and form liquid-crystalline mesophases in a temperature range which is favorable located for electrooptical use.

The invention thus relates to the compounds of the formula I and to the use of the compounds of the formula I as components of liquid-crystalline media, to liquid-crystalline media containing at least one compound of the formula I, and to electrooptical displays which contain media of this type.

Above and below, n, A, r, X and Z are as defined, unless expressly stated otherwise, Cy is 1,4-cyclohexylene and Ph is 1,4-phenylene.

In the compounds of the formula I, the alkyl groups $C_nH_{2n+1}$ are preferably straight-chain. Accordingly, $C_nH_{2n+1}$ is methyl, ethyl, n-propyl, n-butyl, n-pentyl, n-hexyl or n-heptyl. n is preferably 2, 3, 4 or 5.

Compounds of the formula I containing branched alkyl groups may occasionally be of importance due to better solubility in the customary liquid-crystalline base materials, but in particular as chiral dopes if they are optically active. Branched groups of this type generally contain not more than one chain branch. Preferred branched alkyl radicals are isopropyl, 2-butyl (=1-methylpropyl), isobutyl (=2-methylpropyl), 2-methylbutyl, isopentyl (=3-methylbutyl), 2-methylpentyl, 3-methylpentyl or 2-heptyl (=1-methylhexyl).

The radical

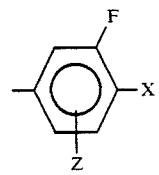

is preferably

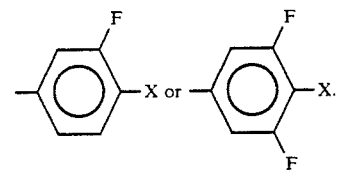

X is preferably F, Cl, —CF₃, OCHF₂ or —OCF₃.

Particular preference is given to the compounds of the sub-formulae below:

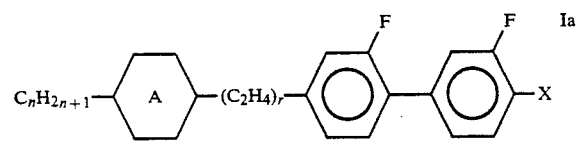

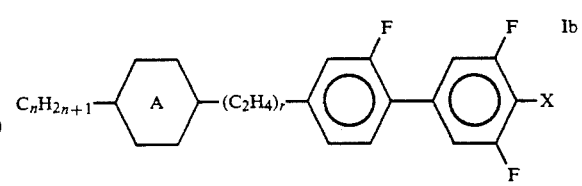

in which X is F, Cl, —CF₃, —CHF₂, —OCF₃ or —OCHF₂.

In addition, the precursors of the compounds of the formula I are prepared by methods known per se, as described in the literature (for example in the standard works such as Houben-Weyl, Methoden der Organischen Chemie [Methods of Organic Chemistry], Georg-Thieme-Verlag, Stuttgart), to be precise under reaction conditions which are known and suitable for said reactions, Use may also be made here of variants which are known per se, but are not described here in greater detail.

If desired, the starting materials can also be prepared in situ by not isolating them from the reaction mixture, instead immediately reacting them further to give the compounds of the formula I.

The compounds of the formula I can be prepared by transition metal-catalyzed coupling reactions which are known per se (cf. E. Poetsch, Kontakte 1988 (2), p. 15), for example in accordance with the synthesis schemes below. Some of the precursors are known, and all can be prepared by coupling reactions known from the literature.

Some of the bromobenzene derivatives used as starting materials are known and some can be prepared without difficulties from compounds known from the literature by standard methods of organic chemistry. For example, the $OCF_3$ or $OCHF_2$ compounds are obtainable from the corresponding phenols and the $CF_3$ or CN compounds from the corresponding benzoic acids, in both cases by known methods. Compounds of the formula

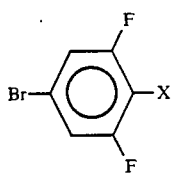

or the corresponding monofluorinated compounds are obtainable, for example, from the known precursors where $X=H$ by lithiation at low temperatures and subsequent reaction with a suitable electrophile.

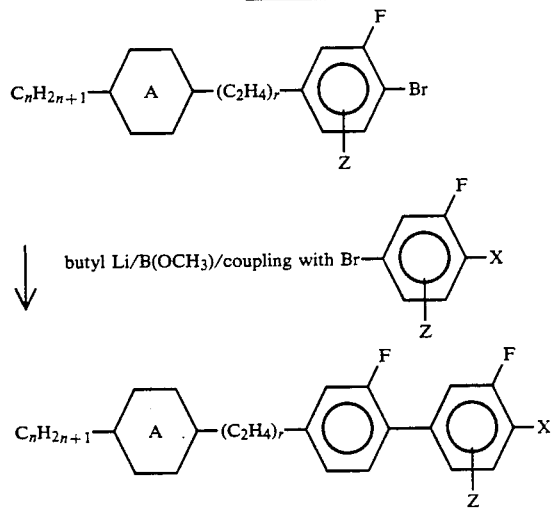

Scheme 1

Scheme 2

The liquid-crystalline media according to the invention preferably contain 2 to 40, in particular 4 to 30, components as further constituents besides one or more compounds according to the invention. These media very particularly preferably contain 7 to 25 components besides one or more compounds according to the invention. These further constituents are preferably selected from nematic or nematogenic (monotropic or isotropic) substances, in particular substances from the classes of the biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid and of cyclohexylcyclohexanecarboxylic acid, phenylcyclohexanes, cyclohexylbiphenyls, phenylcyclohexylcyclohexanes, cyclohexylcyclohexanes, cyclohexylcyclohexenes, cyclohexylcyclohexylcyclohexenes, 1,4-bis-cyclohexylbenzenes, 4,4'-bis-cyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl2-cyclohexylethanes, 1-cyclohexyl-2-(4-phenylcyclohexyl)ethanes, 1-cyclohexyl-2-biphenylylethanes, 1-phenyl-2-cyclohexylphenylethanes and tolans.

The 1,4-phenylene groups in these compounds may also be fluorinated.

The most important compounds suitable as further constituents of media according to the invention can be characterized by the formulae 1, 2, 3, 4 and 5:

| | |
|---|---|
| R'—L—E—R" | 1 |
| R'—L—COO—E—R" | 2 |
| R'—L—OOC—E—R" | 3 |
| R'—L—CH2CH2—E—R" | 4 |
| R'—L—CC—E—R" | 5 |

In the formulae 1, 2, 3, 4 and 5, L and E, which may be identical or different, are in each case, independently of one another, a bivalent radical from the group formed by —Phe—, —Cyc—, —Phe—Phe, —Phe—Cyc—, —Cyc—Cyc—, —Pyr—, —Dio—, —G—Phe— and —G—Cyc— and their mirror images, where Phe is unsubstituted or fluorinesubstituted 1,4-phenylene, Cyc is trans-1,4-cyclohexylene or 1,4-cyclohexenylene, Pyr is pyrimidine-2,5-diyl or pyridine-2,5-diyl, Dio is 1,3-dioxane-2,5-diyl and G is 2-(trans-1,4-cyclohexyl)ethyl, pyrimidine-2,5-diyl, pyridine-2,5-diyl or 1,3-dioxane-2,5-diyl.

One of the radicals L and E is preferably Cyc, Phe or Pyr. E is preferably Cyc, Phe or Phe-Cyc. The media according to the invention preferably contain one or more components selected from the compounds of the formulae 1, 2, 3, 4 and 5 in which L and E are selected from the group comprising Cyc, Phe and Pyr and simultaneously one or more components selected from the compounds of the formulae 1, 2, 3, 4 and 5 in which one of the radicals L and E is selected from the group comprising Cyc, Phe and Pyr and the other racial is selected from the group comprising —Phe—Phe—, —Phe—Cyc—, —Cyc—Cyc—, —G—Phe— and —G—Cyc—, and optionally one or more components selected from the compounds of the formulae 1, 2, 2, 4 and 5 in which the radicals L and E are selected from the group comprising —Phe—Cyc—, —Cyc—Cyc—, —G—Phe— and —G—Cyc—.

In a smaller sub-group of compounds of the formulae 1, 2, 3, 4 and 5, R' and R" are each, independently of one another, alkyl, alkenyl, alkoxy, alkoxyalkyl, alkenyloxy or alkanoyloxy having up to 8 carbon atoms. This smaller sub-group is called group A below, and the compounds are designated by the sub-formulae 1a, 2a, 3a, Ra and 5a. In most of these compounds R' and R" are different from one another, one of these radicals usually being alkyl, alkenyl, alkoxy or alkoxyalkyl.

In another smaller sub-group of compounds of the formulae 1, 2, 3, 4 and 5, called group B, R" is —F, —Cl or —(O)$_i$CH$_{3-(k+1)}$F$_k$CL$_1$, where i is 0 or 1, and k+1 is 1, 2 or 3; the compounds in which R" has this meaning are designated by the sub-formulae 1b, 2b, 3b, 4b or 5b. Particular preference is given to those compounds of the sub-formulae 1b, 2b, 3b, 4b and 5b in which R" is —F, —Cl, —CF$_3$, —OCHF$_2$ or —OCF$_3$.

In the compounds of the sub-formulae 1b, 2b, 3b, 4b and 5b, R' has the meaning indicated for the compounds of the sub-formulae 1a-5a and is preferably alkyl, alkenyl, alkoxy or alkoxyalkyl.

In a further smaller sub-group of the compounds of the formulae 1, 2, 3, 4 and 5, R" is —CN or —NCS; this sub-group is called group C below, and the compounds of this sub-group are accordingly described by the sub-formulae 1c, 2c, 3c, 4c and 5c. In the compounds of the sub-formulae 1c, 2c, 3c, 4c and 5c, R' has the meaning indicated for the compounds of the sub-formulae 1a-5a and is preferably alkyl, alkoxy or alkenyl.

In addition to the preferred compounds of groups A, B and C, other compounds of the formulae 1, 2, 3, 4 and 5 with other variants of the proposed substituents are also customary. All these substances are obtainable by methods known from the literature or analogously thereto.

Besides compounds of the formula I according to the invention, the media according to the invention preferably contain one or more, preferably, 1, 2, 3 or more, in particular 2, 3, 4 or 5, compounds selected from group A, and/or one or more, preferably 1, 2, 3 or more, in particular 2, 3, 4 or 5, compounds selected from group B and/or one or more, preferably 1, 2, 3 or more, in particular 2, 3, 4 and 5, from group C. The proportions by weight of the compounds from these groups in the media according to the invention are preferably Group A: 0 to 90%, preferably 20 to 90%, in particular 30 to 90%

Group B: 0 to 80%, preferably 10 to 80%, in particular 10 to 65%

Group C: 0 to 80%, preferably 5 to 80%, in particular 5 to 50%, the sum of the proportions by weight of the compounds from groups A and/or B and/or C present in the respective media according to the invention preferably being 5%–90% and in particular 10% to 90%.

the media according to the invention preferably contain 1 to 40%, in particular preferably 5 to 30%, of compounds according to the invention. Further preferred media are those which contain more than 40%, in particular 45 to 90%, of compounds according to the invention. The media preferably contain two, three, four or five compounds according to the invention.

The media according to the invention are prepared in a manner which is customary per se. In general, the components are dissolved in one another, expediently at elevated temperature. By means of suitable additives, the liquid-crystalline phases can be modified in accordance with the invention in a manner such that they can be used in all types of liquid-crystal display elements which have hitherto been disclosed. Additives of this type are known to those skilled in the art and are described in detail in the literature (H. Kelker/R. Hatz, Handbook of Liquid Crystals, Verlag Chemie, Weinheim, 1980). For example, pleochroic dyes can be added for the production of colored guest-host systems, or substances can be added to modify the dielectric anisotropy, the viscosity and/or the orientation of the nematic phases.

EXAMPLES

The examples below are intended to illustrate the invention without representing a limitation. mp.=melting point, cp.=clear point. Above and below, percentages are percent by weight; all temperatures are indicated in degrees Celsius. "Customary work-up" means that water is added, the mixture is extracted with methylene chloride, the organic phase is separated off, dried and evaporated, and the product is purified by crystallization and/or chromatography.

In addition, the abbreviations have the following meanings:

C: crystalline-solid state, S: smectic phase ( the index characterizes the phase type), N: nematic state, Ch: cholesteric phase, I: isotropic phase. The number between two symbols indicates the conversion temperature in degrees Celsius.

DAST: diethylaminosulfur trifluoride
DCC: dicyclohexylcarbodiimide
DDQ: dichlorodicyanobenzoquinone
DIBALH: diisobutylaluminum hydride
DMSO: dimethyl sulfoxide
POT: potassium tertiary-butanolate
THF: tetrahydrofuran
pTSOH: p-toluenesulfonic acid

EXAMPLE 1

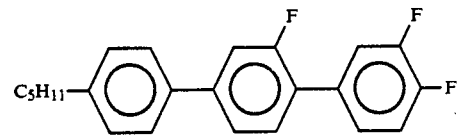

↑
1. −H₂O
2. Chloranil

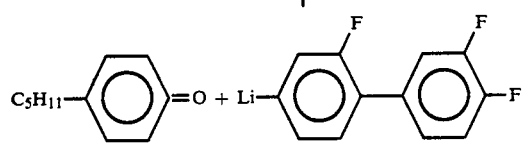

0.1 m of the cyclohexene compound obtained by dehydration of the alcohol (cf. the above scheme) are refluxed for 6 hours in 500 ml of toluene with 0.4 m of chloranil. Extractive work-up and customary purification gives the target product, C 67 S$_A$ 73 N 87.7 I, Δε = +11.48

EXAMPLES 2 TO 34

The following compounds of the formula I (r=O-/A=Ph) are obtained analogously to Example 1

| | n | X | Z |
|---|---|---|---|
| (2) | 2 | —CF₃ | H |
| (3) | 5 | —CF₃ | H |
| (4) | 4 | —CF₃ | H |
| (5) | 5 | F | H |
| (6) | 2 | F | H |
| (7) | 3 | F | H |
| (8) | 5 | Cl | H |
| (9) | 2 | Cl | H |
| (10) | 3 | Cl | H |
| (11) | 5 | Cl | F |
| (12) | 2 | Cl | F |
| (13) | 3 | Cl | F |
| (14) | 5 | F | F |
| (15) | 2 | F | F |
| (16) | 3 | F | F |
| (17) | 2 | —OCF₃ | H |
| (18) | 3 | —OCF₃ | H |
| (19) | 5 | —OCF₃ | H |
| (20) | 2 | —OCF₃ | F |
| (21) | 3 | —OCF₃ | F |
| (22) | 5 | —OCF₃ | F |
| (23) | 2 | —CF₃ | F |
| (24) | 3 | —CF₃ | F |
| (25) | 5 | —CF₃ | F |
| (26) | 2 | OCF₂H | H |
| (27) | 3 | OCF₂H | H |
| (28) | 5 | OCF₂H | H |
| (29) | 2 | OCF₂H | F |
| (30) | 3 | OCF₂H | F |
| (31) | 5 | OCF₂H | F |
| (32) | 4 | F | F |
| (33) | 6 | F | F |
| (34) | 7 | F | F |

EXAMPLE 35

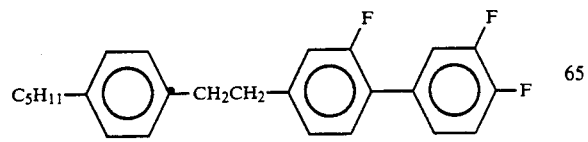

0.05 m of 3,4-difluorobromobenzene, 0.05 m of p-[2-(trans-4-n-pentylcyclohexyl)ethyl]-o-fluorophenylboric acid and 1 g of tetrakistriphenylphosphinepalladium(O) catalyst are dissolved in 100 ml of toluene and 40 ml of ethanol, and 50 ml of 2 m Na₂CO₃ solution are added. The mixture is refluxed for 4 hours and then worked up by extraction. Chromatography and crystallization of the crude material gives the clean product.

EXAMPLES 36–83

The following compounds of the formula I (r=2) are obtained analogously to Example 35

| | n | X | A | Z |
|---|---|---|---|---|
| (36) | 2 | CF₃ | Cy | H |
| (37) | 3 | CF₃ | Cy | H |
| (38) | 5 | CF₃ | Cy | H |
| (39) | 2 | CF₃ | Ph | H |
| (40) | 3 | CF₃ | Ph | H |
| (41) | 5 | CF₃ | Ph | H |
| (42) | 2 | CF₃ | Cy | F |
| (43) | 3 | CF₃ | Cy | F |
| (44) | 5 | CF₃ | Cy | F |
| (45) | 2 | CF₃ | Ph | F |
| (46) | 3 | CF₃ | Ph | F |
| (47) | 5 | CF₃ | Ph | F |
| (48) | 2 | F | Cy | H |
| (49) | 3 | F | Cy | H, C 39 N 61.9 I, Δε = +8.6 |
| (50) | 7 | F | Cy | H |
| (51) | 2 | F | Ph | H |
| (52) | 3 | F | Ph | H |
| (53) | 5 | F | Ph | H |
| (54) | 2 | F | Cy | F |
| (55) | 3 | F | Cy | F, C 38.0 I |
| (56) | 5 | F | Cy | F |
| (57) | 2 | F | Ph | F |
| (58) | 3 | F | Ph | F |
| (59) | 5 | F | Ph | F |
| (60) | 2 | Cl | Cy | H |
| (61) | 3 | Cl | Cy | H, C 51.4 N 96.8 I |
| (62) | 5 | Cl | Cy | H |
| (63) | 2 | Cl | Ph | H |
| (64) | 3 | Cl | Ph | H |
| (65) | 5 | Cl | Ph | H |
| (66) | 2 | Cl | Ph | F |
| (67) | 3 | Cl | Ph | F |
| (68) | 5 | Cl | Ph | F |
| (69) | 2 | Cl | Cy | F |
| (70) | 3 | Cl | Cy | F |
| (71) | 5 | Cl | Cy | F |
| (72) | 2 | OCF₃ | Cy | H |
| (73) | 3 | OCF₃ | Cy | H |
| (74) | 5 | OCF₃ | Cy | H |
| (75) | 2 | OCF₃ | Ph | H |
| (76) | 3 | OCF₃ | Ph | H |
| (77) | 5 | OCF₃ | Ph | H |
| (78) | 2 | OCF₃ | Ph | F |
| (79) | 3 | OCF₃ | Ph | F |
| (80) | 5 | OCF₃ | Ph | F |
| (81) | 2 | OCF₃ | Cy | F |
| (82) | 3 | OCF₃ | Cy | F |
| (83) | 5 | OCF₃ | Cy | F |

EXAMPLE 84

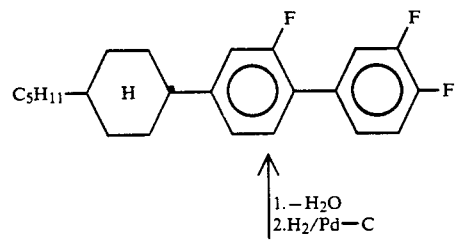

↑
1. −H₂O
2. H₂/Pd—C

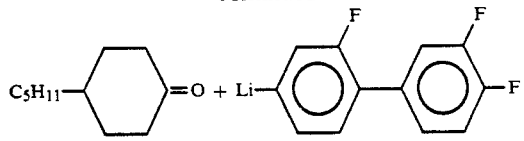

0.1 m of the cyclohexene compound obtained by dehydration of the alcohol (cf. the above scheme) are hydrogenated to saturation with 5 g of Pd/C (5% in 500 ml of toluene). Extractive work-up and customary purification give the target product.

EXAMPLES 85–114

The following compounds of the formula I (r=0-/A=Cy) are obtained analogously to Example 84.

| | n | X | Z |
|---|---|---|---|
| (85) | 2 | $CF_3$ | H |
| (86) | 3 | $CF_3$ | H |
| (87) | 7 | $CF_3$ | H |
| (88) | 2 | $CF_3$ | F |
| (89) | 3 | $CF_3$ | F |
| (90) | 5 | $CF_3$ | F |
| (91) | 2 | F | F |
| (92) | 3 | F | F |
| (93) | 5 | F | F |
| (94) | 2 | F | H |
| (95) | 3 | F | H |
| (96) | 5 | F | H |
| (97) | 2 | Cl | H |
| (98) | 3 | Cl | H |
| (99) | 5 | Cl | H |
| (100) | 2 | Cl | F |
| (101) | 3 | Cl | F |
| (102) | 5 | Cl | F |
| (103) | 2 | $OCF_3$ | F |
| (104) | 3 | $OCF_3$ | F |
| (105) | 5 | $OCF_3$ | F |
| (106) | 2 | $OCF_3$ | H |
| (107) | 3 | $OCF_3$ | H |
| (108) | 5 | $OCF_3$ | H |
| (109) | 2 | $OCF_2H$ | H |
| (110) | 3 | $OCF_2H$ | F |
| (111) | 5 | $OCF_2H$ | F |
| (112) | 2 | $OCF_2H$ | F |
| (113) | 3 | $OCF_2H$ | F |
| (114) | 5 | $OCF_2H$ | F |

EXAMPLE A

A liquid-crystalline mixture comprising
10.36% of 2-[trans-4-(trans-4-propylcyclohexyl)cyclohexyl]-1-(4-chlorophenyl)ethane
14.36% of 2-[trans-4-(trans-4-pentylcyclohexyl)cyclohexyl]-1-(4-chlorophenyl)ethane
10.44% of 2-[trans-4-(trans-4-pentylcyclohexyl)cyclohexyl]-1-(3-fluoro-4-chlorophenyl)ethane
9.57% of 4-(trans-4-propylcyclohexyl)benxonitrile
10.36% of 4-[2-(trans-4-propylcyclohexyl)ethyl]benzonitrile
9.58% of 4'-ethyl-4-cyanobiphenyl
4.78% of 4-(trans-4-pentylcyclohexyl)phenyl trans4-(trans-4-propylcyclohexyl)cyclohexyl-1-carboxylate
7.99% of 4-pentylphenyl trans-4-propylcyclohexyl1-carboxylate
2.40% of 4-cyano-3-fluorophenyl 4-ethylbenzoate
20.16% of 2-(trans-4-propylcyclohexyl)-1-(2,3',4'-trifluorobiphenyl-4-yl)ethane has C<−10 N 89.1 I; viscosity (20° C.): 23.7 cSt; n: 0.1286.

The threshold voltage ($V_{th}$) of this mixture, measured in an STN cell with 240° twist, is 2.22 volts.

We claim:
1. A 4,4'-disubstituted 2', 3-difluorobiphenyl of formula Ia

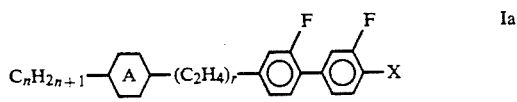

wherein

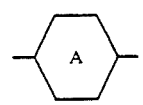

is trans-1,4-cyclohexylene or 1,4-phenylene,
n is 1-7,
r is 0, and
X is F, Cl or —$CF_3$.

2. A liquid-crystalline medium having at least two liquid-crystalline components, the improvement wherein at least one of said components is a compound of formula Ia according to claim 1.

3. In an electrooptical display device having a liquid-crystal cell containing a liquid-crystalline medium, the improvement wherein said liquid-crystal cell contains a medium according to claim 2.

4. A method of generating an electrooptical display using an electrooptical display device, the improvement wherein said device is a device according to claim 3.

5. A compound according to claim 1, wherein X is F.
6. A compound according to claim 1, wherein X is Cl.
7. A compound according to claim 1, wherein X is —$CF_3$.
8. A compound according to claim 1, wherein n is 2–5.
9. A compound according to claim 1, wherein ring A is trans-1,4-cyclohexylene.
10. A compound according to claim 1, wherein ring A is 1,4-phenylene.

* * * * *